(12) United States Patent
Hu (10) Patent No.: US 10,575,799 B2
(45) Date of Patent: Mar. 3, 2020

(54) METHOD AND APPARATUS FOR COLLECTING DATA

(71) Applicant: SHENYANG NEUSOFT MEDICAL SYSTEMS CO., LTD., Shenyang (CN)

(72) Inventor: Xiaoqing Hu, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 110 days.

(21) Appl. No.: 15/960,237

(22) Filed: Apr. 23, 2018

(65) Prior Publication Data

US 2018/0303443 A1 Oct. 25, 2018

(30) Foreign Application Priority Data

Apr. 24, 2017 (CN) .......................... 2017 1 0271346

(51) Int. Cl.
  *A61B 6/00* (2006.01)
  *A61B 6/03* (2006.01)
  (Continued)

(52) U.S. Cl.
  CPC ............ *A61B 6/4233* (2013.01); *A61B 6/032* (2013.01); *A61B 6/52* (2013.01); *A61B 6/5205* (2013.01);
  (Continued)

(58) Field of Classification Search
  CPC ......... A61B 6/5205; A61B 5/562; H03M 1/12
  See application file for complete search history.

(56) References Cited

U.S. PATENT DOCUMENTS

| 4,458,267 A | 7/1984 | Dolazza |
| 9,743,024 B2 * | 8/2017 | Tyrrell .................... H04N 5/335 |

(Continued)

FOREIGN PATENT DOCUMENTS

| CN | 1449722 A | 10/2003 |
| CN | 101006925 A | 8/2007 |

(Continued)

OTHER PUBLICATIONS

State Intellectual Property Office of the People's Republic of China, Office Action and Search Report Issued in Application No. 201710271346.9, dated Dec. 18, 2019, 11 pages. (Submitted with Machine Translation).

*Primary Examiner* — Kenneth J Malkowski
(74) *Attorney, Agent, or Firm* — McCoy Russell LLP (57) ABSTRACT

An apparatus for collecting data is provided. According to an example, the apparatus for collection data may include: n number of detector arrays, n number of DAS circuits and a back-end processor. Each of the DAS circuits may include an analog-to-digital converter and a front-end processor coupled with the analog-to-digital converter. Each of front-end processors is coupled with the back-end processor via an independent transmission line. For each of the detector arrays, the detector array may be configured to output analog signals based on detected scanning rays penetrating through a subject. The analog-to-digital converter may be configured to perform an analog-to-digital conversion on the analog signals to generate raw data. The front-end processor may be configured to logarithmically compress the raw data and transmit the logarithmically-compressed raw data to the back-end processor via the transmission line.

16 Claims, 4 Drawing Sheets

(51) Int. Cl.
    *G01N 23/046*     (2018.01)
    *G01T 1/16*     (2006.01)
    *H03M 1/12*     (2006.01)
    *H04N 5/32*     (2006.01)

(52) U.S. Cl.
    CPC ............. *G01N 23/046* (2013.01); *G01T 1/16* (2013.01); *H03M 1/12* (2013.01); *H04N 5/32* (2013.01)

(56) References Cited

U.S. PATENT DOCUMENTS

2007/0075888 A1*   4/2007   Kelly .................. H03M 1/145
                                                  341/155
2016/0295145 A1*  10/2016   Nitta .................. H03M 1/1023

FOREIGN PATENT DOCUMENTS

| CN | 101576514 A | 11/2009 |
|---|---|---|
| CN | 201510294 U | 6/2010 |
| CN | 102253063 A | 11/2011 |
| CN | 102525532 A | 7/2012 |
| CN | 102970934 A | 3/2013 |
| CN | 103330571 A | 10/2013 |
| JP | H05130988 A | 5/1993 |

* cited by examiner

FIG. 5
METHOD AND APPARATUS FOR COLLECTING DATA

CROSS REFERENCE TO RELATED APPLICATIONS

This application claims priority to Chinese Patent Application No. 201710271346.9 filed on Apr. 24, 2017, the entire contents of which is incorporated herein by reference in its entirety for all purposes.

TECHNICAL FIELD

The present disclosure relates to a method and an apparatus for collecting data.

BACKGROUND

A Computed Tomography (CT) device is to perform CT scan on a subject, such as a human body, with scanning rays, such as X-rays. Due to different densities of a subject, such as a human body, the scanning rays, such as x-rays, may have different penetration rates. A CT image may be reconstructed by receiving the scanning rays penetrating through the subject, converting the scanning rays into electric signals and then processing the electric signals with a computer.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

Figure 1:
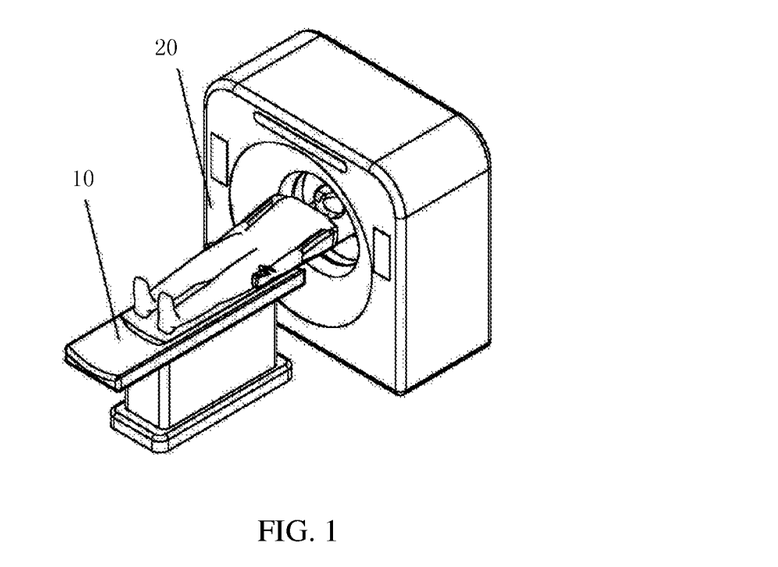
FIG. 1 is a schematic diagram illustrating a structure of a CT device according to an example of the present disclosure.

FIG. 1 illustrates a structure of a CT device according to an example of the present disclosure. The CT device includes a scanning bed 10 for placing a subject and a scanning host 20 rotating around the scanning bed 10. The scanning host 20 includes a data collection apparatus for collecting scanning rays penetrating through the subject. The data collection apparatus may be referred to as the apparatus for collecting data hereinafter.

In an example, the apparatus for collecting data includes at least one detector array, at least one data acquisition system (DAS) circuit and one back-end processor. The at least one DAS circuit corresponds to the at least one detector array. Each DAS circuit may include an analog-to-digital (AD) converter and a front-end processor coupled with the analog-to-digital converter. Each analog-to-digital converter is coupled with a corresponding detector array. Each front-end processor is coupled with the back-end processor via an independent transmission line for transmitting data.

In an example, a process for collecting data with the above data collection apparatus may be as follows: after scanning rays, such as cone-shaped X-rays are emitted from a bulb tube, the scanning rays penetrate through the subject, such as a human body and then are received by the detector arrays; each of the detector arrays converts the received scanning rays into analog signals and then outputs the analog signals to the corresponding DAS circuit; the analog-to-digital converter in each of the DAS circuits performs an analog-to-digital conversion on the received analog signals to generate raw data and output the raw data to the front-end processor in the DAS circuit; and the front-end processor logarithmically compresses the raw data and transmits the logarithmically compressed raw data to the back-end processor via a transmission line.

In an example, each detector array includes a plurality of rows of detectors. In this way, raw data from a plurality of slices may be collected simultaneously in a rotation period, thereby effectively ensuring imaging continuity of a reconstructed CT image and effectively avoiding motion artifacts when a motion object, such as a heart is scanned. Further, the speed of collecting data can be effectively increased, scanning time can be shortened and radiation to the human body can be reduced.

However, the multi-row detector array may cause a higher transmission rate of the transmission line between the front-end processor and the back-end processor. For example, a detector array may include 256 or 512 rows of detectors where each of the rows has 16 channels. A transmission line between each of the front-end processors and the back-end processor may have a transmission rate of up to 800 megabits per second. Due to the relatively high transmission rate, relatively high requirements will be proposed for the transmission bandwidth of the transmission line, for example, the transmission line has the relatively high transmission bandwidth. And margin size of the transmission bandwidth may have direct impact on the reliability of the CT device. Also, the transmission line between the front-end processor and the back-end processor may include a cable. Electric connection may be provided by a connector at two ends of the cable. An impedance difference between the cable and the connector may cause reflection of transmission data and even may limit the transmission bandwidth of the transmission line.

To meet transmission bandwidth requirements of the transmission line, in a first manner, a high frequency cable with relatively high transmission bandwidth is employed as the transmission line. However, in the first manner, it is ensured that the impedance of the cable is substantially consistent with the impedance of the connector. Each of the front-end processors are coupled with the back-end processor by an independent high frequency cable. In this way, precious wiring space is occupied and costs are increased. In a second manner, a number of transmission lines are increased. However, in the second manner, the front-end processor and the back-end processor have more input/output pins compared with the first manner, thereby increasing costs. For example, when the data collection apparatus includes 45 front-end processors, if a group of differential signal lines as the transmission line is added between each of the front-end processors and the back-end processor, the back-end processor increases 90 input/output pins. In this way, for the back-end processor, costs of pins are increased and a plurality of processing chips may even be needed to match the pins.

The present disclosure provides a method and an apparatus for collecting data. When the method and the apparatus for collecting data are applied, the transmission bandwidth requirements of the transmission line can be met, the occupied wiring space can be effectively decreased and costs can be further lowered.

To make a person skilled in the art better understand the technical solutions of the present disclosure, the technical solutions of the present disclosure will be described clearly and fully below in combination with drawings in the examples of the present disclosure. It is apparent that the described examples are merely part of examples of the present disclosure rather than all examples. Other examples achieved by those of ordinary skill in the art based on the examples in the present disclosure without paying creative work shall all fall into the scope of protection of the present disclosure.

Figure 2:
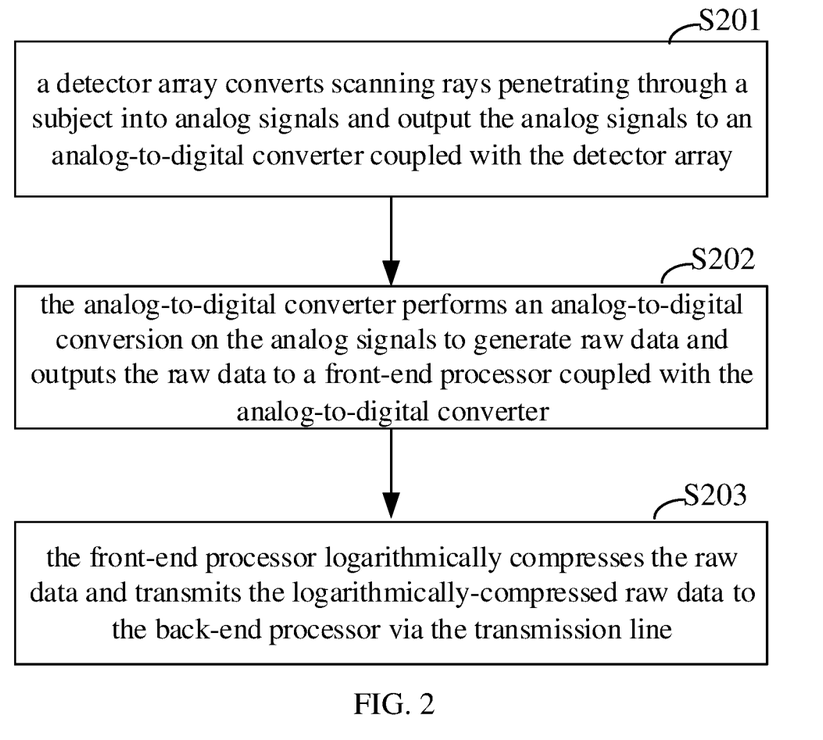
FIG. 2 is a flowchart illustrating a method of collecting data according to an example of the present disclosure.

FIG. 2 is a flowchart illustrating a method of collecting data according to an example of the present disclosure. The method of collecting data may be applied to an apparatus for collecting data. The apparatus for collecting data is located in a CT device and includes at least one detector array, at least one analog-to-digital converter, at least one front-end processor, and one back-end processor.

Figure 3:
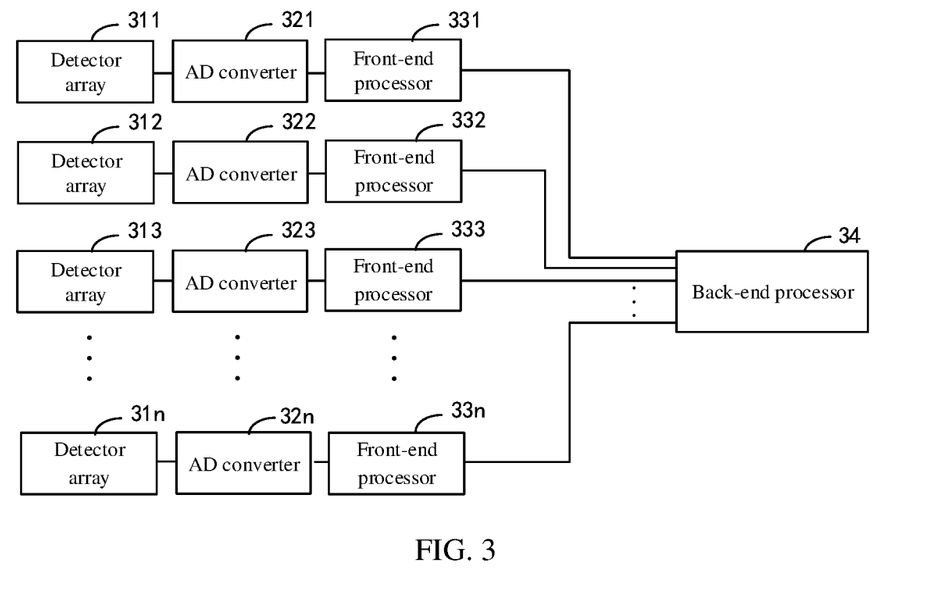
FIG. 3 is a schematic diagram illustrating a structure of an apparatus for collecting data according to an example of the present disclosure.

FIG. 3 is a schematic diagram illustrating a structure of an apparatus for collecting data according to an example of the present disclosure. The apparatus for collecting data includes n number of detector arrays: detector array 311, detector array 312, detector array 313, . . . and detector array 31n; n number of analog-to-digital converters: analog-to-digital converter 321, analog-to-digital converter 322, analog-to-digital converter 323, . . . and analog-to-digital converter 32n; n number of front-end processors: front-end processor 331, front-end processor 332, front-end processor 333, . . . and front-end processor 33n; and a back-end processor 34. Where n is an integer greater than or equal to 1. The n number of detector arrays, the n number of analog-to-digital converters, and the n number of front-end processors are set correspondingly one to one. For example, the detector array 311, the analog-to-digital converter 321 and the front-end processor 331 are set correspondingly, that is, the detector array 311 is coupled with the analog-to-digital converter 321, and the analog-to-digital converter 321 is coupled with the front-end processor 331. Each of the front-end processors is coupled with the back-end processor 34 via an independent transmission line for transmitting data. It is noted that the number of the analog-to-digital converters is not limited to n, for example, the detector array 311 may be coupled with two analog-to-digital converters and the two analog-to-digital converters may be coupled with the front-end processor 331.

The method of collecting data may include the following blocks:

At block S201, a detector array converts scanning rays penetrating through a subject into analog signals and output the analog signals to an analog-to-digital converter coupled with the detector array.

After scanning rays, such as cone-shaped X-rays are emitted from the bulb tube, each of the detector arrays receives the scanning rays penetrating through the subject. Each of the detector arrays converts the received scanning rays into analog signals and output the analog signals to the analog-to-digital converter for performing an analog-to-digital conversion.

When the apparatus for collecting data includes n number of detector arrays 311-31n, each of the n number of detector arrays 311-31n may convert received scanning rays into analog signals and output the analog signals to the corresponding analog-to-digital converter. As shown in FIG. 3, the detector array 311 outputs the analog signals to the analog-to-digital converter 321 coupled with the detector array 311.

At block S202, the analog-to-digital converter performs an analog-to-digital conversion on the analog signals to generate raw data and outputs the raw data to a front-end processor coupled with the analog-to-digital converter.

The analog-to-digital converter may obtain digital signals by performing the analog-to-digital conversion on the analog signals. The digital signals are the generated raw data.

When the apparatus for collecting data includes n number of analog-to-digital converters 321-32n, each of the analog-to-digital converters 321-32n may perform the analog-to-digital conversion on the received analog signals to generate raw data and output the generated raw data to the corresponding front-end processor. As shown in FIG. 3, the analog-to-digital converter 321 outputs the generated raw data to the front-end processor 331 coupled with the analog-to-digital converter 321.

At block S203, the front-end processor logarithmically compresses the raw data and transmits the logarithmically-compressed raw data to the back-end processor via the transmission line.

In an example, after receiving the logarithmically compressed raw data, the back-end processor 34 may output the logarithmically-compressed raw data to a computer for reconstructing an image. In this way, the reconstructed image is obtained.

When the apparatus for collecting data includes n number of front-end processors 331-33n, each of the n number of front-end processors 331-33n may logarithmically compress the received raw data and transmit the logarithmically-compressed raw data to the back-end processor via the transmission line between the front-end processor and the back-end processor. As shown in FIG. 3, the front-end processor 331 logarithmically compresses the received raw data and transmits the logarithmically compressed raw data to the back-end processor 34 via the transmission line between the front-end processor 331 and the back-end processor 34. The back-end processor 34 may synchronically receive and latch the logarithmically compressed raw data transmitted by the n number of front-end processors 331-33n.

The logarithmic compression refers to performing logarithm-taking processing for raw data with a logarithm function. It is noted that the logarithmic compression is a data processing operation to obtain data for reconstructing the image and may be performed by the back-end processor. But in the present disclosure, the front-end processor performs the logarithmic compression and then transmits the logarithmically compressed data to the back-end processor. In this way, no new data processing operation is increased and data volume transmitted between the front-end processor and the back-end processor is reduced at a relatively large extent, thereby effectively reducing the transmission rate of the transmission line between the front-end processor and the back-end processor. For example, if data volume of the raw data before the logarithmic compression is about 24 bits and the transmission rate is about 800 megabits/second, the data volume of the raw data after logarithmic compression is reduced to about 16 bits. It is found that there is a reduction of ⅓ of the data volume transmitted in unit time. Therefore, the transmission rate is also lowered to less than about 600 megabits/second.

As can be seen from the above technical solution, in the present disclosure, each of the front-end processors does not directly transmit the raw data to the back-end processor but logarithmically compresses the raw data and then transmits the logarithmically compressed raw data to the back-end processor. Since the logarithmic compression is a data processing operation to obtain data for reconstructing the image, the method of collecting data in the present disclosure does not increase new data processing operation and also can reduce the transmission rate of the transmission line, resulting in overall improved processing efficiency. Further, requirements for transmission bandwidth can be met. Therefore, the method of collecting data in the present disclosure does not use a high frequency cable with relative high transmission bandwidth nor increase the number of transmission lines. At this case, occupied wiring space can be effectively reduced and costs can also be effectively lowered. In addition, for the back-end processor, a reduced transmission rate between the back-end processor and a corresponding front-end processor may reduce design complexity of the back-end processor.

In an example, in the front-end processor and the back-end processor, due to reasons such as egress direction of a port and a physical position of hardware and so on, the front-end processor and the back-end processor may be difficult to be coupled with each other. To make the connection between the front-end processor and the back-end processor easier, the front-end processor may transmit the logarithmically-compressed raw data to the back-end processor via a plurality of flexible cables or a circuit board containing a flexible portion.

In an example, the front-end processor and the back-end processor are both implemented by a Field Programmable Gate Array (FPGA). How the front-end processor and the back-end processor are implemented by a FPGA will be described below with an example.

Figure 4:
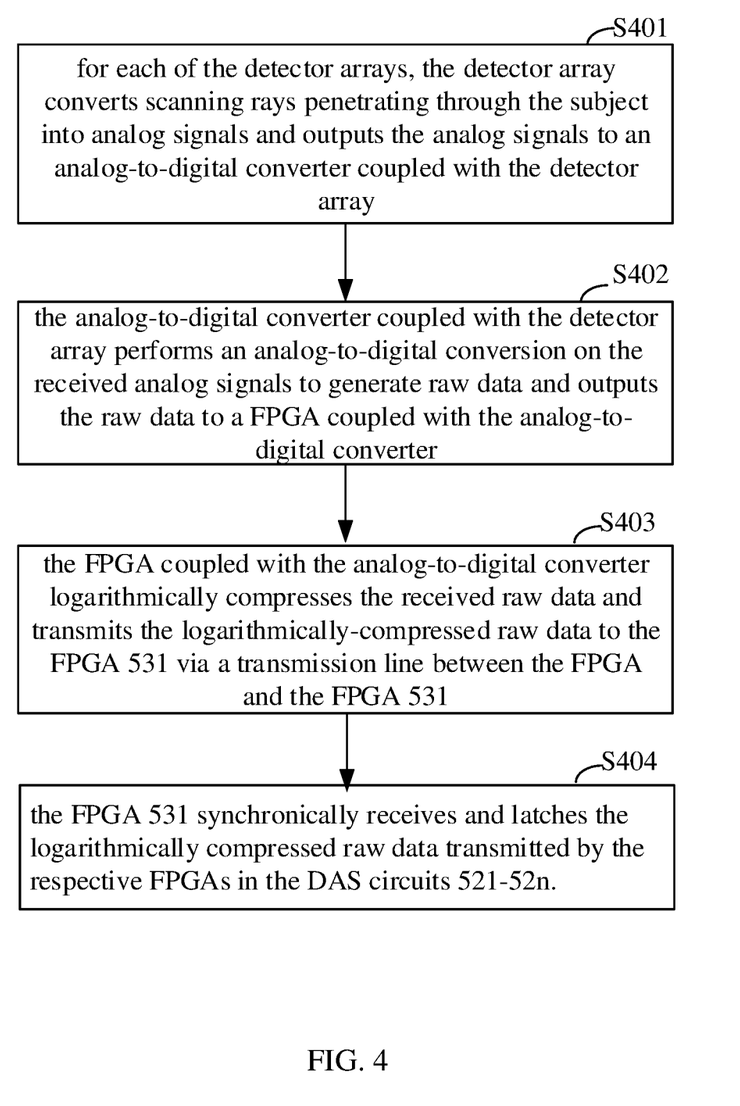
FIG. 4 is a flowchart illustrating a method of collecting data according to another example of the present disclosure.

FIG. 4 is a flowchart illustrating a method of collecting data according to another example of the present disclosure. The method of collecting data may be applied to the apparatus for collecting data shown in FIG. 5. The apparatus for collecting data is located in a CT device, for example, in a scanning host rotating around a scanning bed. The apparatus for collecting data may include n number of detector arrays: detector array 511, detector array 512, detector array 513, . . . and detector array 51*n*; n number of data acquisition system (DAS) circuits set correspondingly to the n number of detector arrays: DAS circuit 521, DAS circuit 522, DAS circuit 523, . . . and DAS circuit 52*n*; and a back-end processor 53. Where n is an integer greater than 1. Each of the DAS circuits 521-52*n* may include one of analog-to-digital converters 5211-52*n*1 and one of FPGAs 5212-52*n*2. The back-end processor 53 may include an FPGA 531 and a clock generator 532. The analog-to-digital converter in each of DAS circuits 521-52*n* is coupled with the corresponding detector array 511-51*n*. An independent transmission line for transmitting data is provided between the FPGA in each of the DAS circuits 521-52*n* and the FPGA 531.

The method of collecting data may include the following blocks:

At block S401, for each of the detector arrays, the detector array may convert scanning rays penetrating through the subject into analog signals and output the analog signals to an analog-to-digital converter coupled with the detector array.

Figure 5:
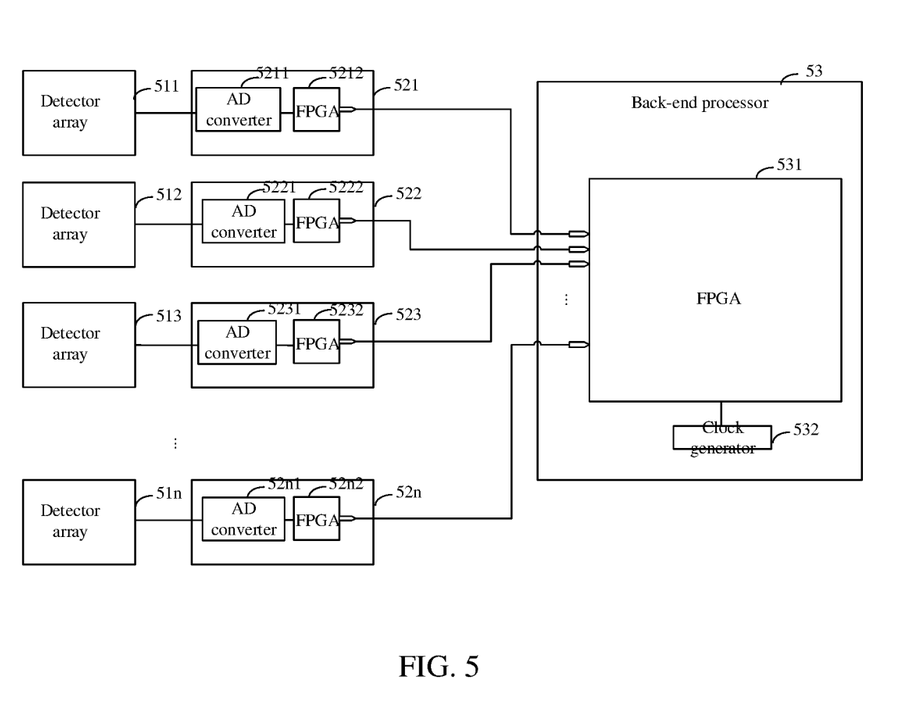
FIG. 5 is a schematic diagram illustrating a structure of an apparatus for collecting data according to another example of the present disclosure.

In an example, after scanning rays such as cone-shaped X-rays are emitted from a bulb tube, the scanning rays penetrate through the subject and then are received by each of the detector arrays 511-51*n*. Each of the detector arrays 511-51*n* may include a plurality of rows of detectors, for example, 256 rows of detectors or 512 rows of detectors and each row of detectors may include 16 channels.

For example, the detector array 511 converts the scanning rays received by the detector array 511 into analog signals and outputs the analog signals to the analog-to-digital converter 5211 in the DAS circuit 521; the detector array 512 converts the scanning rays received by the detector array 512 into analog signals and outputs the analog signals to the analog-to-digital converter 5221 in the DAS circuit 522 and so on.

At block S402, the analog-to-digital converter coupled with the detector array may perform an analog-to-digital conversion on the received analog signals to generate raw data and output the raw data to a FPGA coupled with the analog-to-digital converter.

In an example, the analog-to-digital converter 5211 in the DAS circuit 521 performs an analog-to-digital conversion on the received analog signals to generate raw data and outputs the raw data to the FPGA 5212 in the DAS circuit 521; the analog-to-digital converter 5221 in the DAS circuit 522 performs an analog-to-digital conversion on the received analog signals to generate raw data and outputs the raw data to the FPGA 5222 in the DAS circuit 522 and so on.

At block S403, the FPGA coupled with the analog-to-digital converter may logarithmically compress the received raw data and transmit the logarithmically-compressed raw data to the FPGA 531 via a transmission line between the FPGA and the FPGA 531.

In an example, the FPGA 5212 in the DAS circuit 521 logarithmically compresses the received raw data and transmits the logarithmically compressed raw data to the FPGA 531 via an independent transmission line between the DAS circuit 521 and the FPGA 531; the FPGA 5222 in the DAS circuit 522 logarithmically compresses the received raw data and transmits the logarithmically compressed raw data to the FPGA 531 via an independent transmission line between the DAS circuit 522 and the FPGA 531 and so on.

Each of the FPGAs 5212-52*n*2 in the DAS circuits 521-52*n* may be a FPGA with a memory storing a logarithm table. Each of the FPGAs 5212-52*n*2 in the DAS circuits 521-52*n* may logarithmically compress the received raw data by searching the logarithm table.

At block S404, the FPGA 531 may synchronically receive and latch the logarithmically compressed raw data transmitted by the respective FPGAs in the DAS circuits 521-52*n*.

The FPGA 531 may provide a clock signal by using the clock generator 532 and synchronically receive and latch the received logarithmically compressed raw data at an edge of the clock signal. After latching the logarithmically compressed raw data, the FPGA 531 may also transmit the latched data to a computer for reconstructing an image. In this way, the reconstructed image may be obtained.

In an example of the present disclosure, because operations performed by the FPGA in each of DAS circuits are same, a configuration equation for the FPGA in each of the DAS circuits is same, thereby effectively reducing design complexity of the entire apparatus for collecting data.

In an example, when all data is stable at an edge of a clock signal, the logarithmically compressed raw data transmitted by the respective DAS circuits may be correctly received. If the transmission rate is higher, higher requirements will be proposed for wiring length of translation line between each of the DAS circuits and the back-end processor, consistency of wiring regulation and circuit manufacturing process of the back-end processor. In an example of the present disclosure, since the FPGA in each of the DAS circuits 521-52$n$ logarithmically compresses the raw data, the transmission bandwidth between each of the DAS circuits 521-52$n$ and the FPGA 531 in the back-end processor 53 is reduced. For example, if data volume of the raw data before the logarithmic compression is about 24 bits and the transmission rate is about 800 megabits/second, the data volume of the raw data after logarithmic compression is reduced to about 16 bits. It is found that there is a reduction of ⅓ of the data volume transmitted in unit time. Therefore, the transmission rate is also lowered to less than about 600 megabits/second. In the present disclosure, a high frequency cable with bandwidth of 600 megabits/second can be used as the transmission line, instead of a high frequency cable with bandwidth of 800 megabits/second. In this way, the wiring space occupied by the DAS circuits can be reduced effectively and costs for the apparatus for collecting data can further be lowered.

Corresponding to the above method examples, the present disclosure further provides corresponding apparatus examples which will be described in details as below.

According to an example of the present disclosure, there is provided an apparatus for collecting data, including a detector array, an analog-to-digital converter, a front-end processor and a back-end processor. The front-end processor and the back-end processor are coupled via a transmission line.

The detector array may be configured to convert scanning rays penetrating through a subject into analog signals and output the analog signals to the analog-to-digital converter coupled with the detector array.

The analog-to-digital converter may be configured to perform an analog-to-digital conversion on the analog signals to generate raw data and output the raw data to the front-end processor coupled with the analog-to-digital converter.

The front-end processor may be configured to logarithmically compress the raw data and transmit the logarithmically compressed raw data to the back-end processor via the transmission line.

The back-end processor may be configured to receive and latch the logarithmically compressed raw data transmitted by the front-end processors.

FIG. 3 illustrates a structure of an apparatus for collecting data according to an example of the present disclosure. The structure may include n number of detector arrays: detector array 311, detector array 312, detector array 313, . . . and detector array 31$n$; n number of analog-to-digital converters: analog-to-digital converter 321, analog-to-digital converter 322, analog-to-digital converter 323, . . . and analog-to-digital converter 32$n$; n number of front-end processors: front-end processor 331, front-end processor 332, front-end processor 333, . . . and front-end processor 33$n$ and a back-end processor 34. Where n is an integer greater than 1. The n number of detector arrays 311-31$n$, the n number of analog-to-digital converters 321-32$n$ and the n number of front-end processors 331-33$n$ are set correspondingly one to one. For example, the detector array 311, the analog-to-digital converter 321 and the front-end processor 331 are set correspondingly, that is, the detector array 311 is coupled with the analog-to-digital converter 321 and the analog-to-digital converter 321 is coupled with the front-end processor 331. Each of the front-end processors 331-33$n$ is coupled with the back-end processor 34 via an independent transmission line for transmitting data.

In an example, each of the front-end processors may include a memory storing a logarithm table and a Field Programmable Gate Array (FPGA).

The FPGA may logarithmically compress the raw data by searching the stored logarithm table.

In an example, the apparatus for collecting data may include n number of detector arrays, n number of DAS circuits respectively coupled with one of the detector arrays and a back-end processor coupled with the n number of DAS circuits. Where n is an integer greater than 1. Each of the DAS circuits includes an analog-to-digital converter and a front-end processor coupled with the analog-to-digital converter. Each of the n number of DAS circuits and the back-end processor is coupled via a transmission line. For example, each of the front-end processors and the back-end processor is coupled via the transmission line. The back-end processor may be configured to synchronically receive and latch logarithmically compressed raw data transmitted by the respective front-end processors in the n number of DAS circuits.

In an example, each of the front-end processor may include an FPGA and a configuration equation for the FPGA in each of the front-end processors is same.

In an example, the transmission line includes a plurality of flexible cables or a circuit board containing a flexible portion.

In an example, the back-end processor may be configured to output the logarithmically compressed raw data to a computer for reconstructing an image.

It may be appreciated by persons skilled in the art that, for convenience and simplicity of description, the specific working process of the apparatus for collecting data as described above may be referred to the corresponding process of the above method examples and will not be repeated herein.

In examples provided in the present disclosure, it should be understood that the apparatus and method disclosed herein may be implemented by other manners. For example, the above apparatus examples are merely illustrative. For example, a plurality of components may be combined or integrated into another system or some features may be neglected or not executed. On the other hand, mutual coupling or direct coupling or communication connection displayed or mentioned herein may include an indirect coupling or a communication connection via some interfaces and may be in the form of electric or mechanical connection or in other forms.

In addition, different components in different examples of the present disclosure may be integrated into one system and may also exist physically and individually and two or more components may also be integrated into one system. The above integrated components may be implemented in the form of hardware or software functional units.

The above examples are used only to describe the technical solutions of the present disclosure rather than limit the present disclosure. Although detailed description is made by referring to the above examples, it should be appreciated by the ordinary persons skilled in the art that the technical solutions described in above examples can be modified or some technical features can be replaced equivalently and these modifications and substitutions are still encompassed into the protection scope of the technical solutions of the present disclosure.

The invention claimed is:

1. A method of collecting data, applied to an apparatus for collecting data, wherein the apparatus for collecting data comprises:
   n number of detector arrays, wherein n is an integer greater than or equal to 1;
   n number of data acquisition system (DAS) circuits respectively coupled with one detector array, wherein each of the DAS circuits comprises an analog-to-digital converter and a front-end processor coupled with the analog-to-digital converter; and a back-end processor coupled with each of the front-end processors, wherein each of the front-end processors is coupled with the back-end processor via an independent transmission line;
   the method comprises:
   for each of the detector arrays, generating, by the detector array, analog signals based on scanning rays which penetrate through a subject and detected by the detector array;
   outputting, by the detector array, the analog signals to the analog-to-digital converter coupled with the detector array;
   performing, by the analog-to-digital converter, an analog-to-digital conversion on the analog signals to generate raw data;
   outputting, by the analog-to-digital converter, the raw data to the front-end processor coupled with the analog-to-digital converter;
   logarithmically compressing, by the front-end processor, the raw data to obtain logarithmically compressed raw data; and transmitting, by the front-end processor, the logarithmically compressed raw data to the back-end processor via the independent transmission line connecting the front-end processor and the back-end processor.

2. The method according to claim 1, wherein each of the front-end processors comprises:
   a memory storing a logarithm table; and a first Field Programmable Gate Array (FPGA) for logarithmically compressing the raw data by searching the logarithm table.

3. The method according to claim 2, wherein each of the front-end processors comprises a same configuration equation as the first FPGA.

4. The method according to claim 1, further comprising:
   synchronically receiving and latching, by the back-end processor, the logarithmically compressed raw data transmitted by the front-end processors.

5. The method according to claim 4, wherein the back-end processor comprises:
   a clock generator for providing a clock signal; and a second FPGA for synchronically receiving and latching the logarithmically compressed raw data transmitted by the front-end processors at an edge of the clock signal.

6. The method according to claim 1, wherein the transmission line comprises a plurality of flexible cables.

7. The method according to claim 1, wherein the transmission line comprises a circuit board containing a flexible portion.

8. The method according to claim 1, further comprising:
   outputting, by the back-end processor, the logarithmically compressed raw data to a computer for reconstructing an image.

9. An apparatus for collecting data, comprising:
   n number of detector arrays, respectively configured to output analog signals based on scanning rays which penetrate through a subject and detected by the detector arrays, wherein n is an integer greater than 1;
   n number of data acquisition system (DAS) circuits respectively coupled with one of the detector arrays, wherein each of the DAS circuits comprises
   an analog-to-digital converter to perform an analog-to-digital conversion on the analog signals to generate raw data, and a front-end processor coupled with the analog-to-digital converter and configured to logarithmically compress the raw data; and a back-end processor coupled with each of front-end processors via an independent transmission line and configured to receive the logarithmically compressed raw data transmitted by each of the front-end processors via the independent transmission line.

10. The apparatus according to claim 9, wherein each of the front-end processor comprises:
    a memory storing a logarithm table; and a first Field Programmable Gate Array (FPGA) for logarithmically compressing the raw data by searching the logarithm table.

11. The apparatus according to claim 10, wherein each of the front-end processors comprises a same configuration equation as the first FPGA.

12. The apparatus according to claim 9, wherein the back-end processor is further configured to:
    synchronically receive and latch the logarithmically compressed raw data transmitted by the respective front-end processors.

13. The apparatus according to claim 9, wherein the back-end processor comprises:
    a clock generator for providing a clock signal; and a second FPGA configured to synchronically receive and latch the logarithmically compressed raw data transmitted by the respective front-end processors at an edge of the clock signal.

14. The apparatus according to claim 9, wherein the transmission line comprises a plurality of flexible cables.

15. The apparatus according to claim 9, wherein the transmission line comprises a circuit board containing a flexible portion.

16. The apparatus according to claim 9, wherein the back-end processor is further configured to output the logarithmically compressed raw data to a computer for reconstructing an image.

* * * * *